United States Patent [19]

Russell

[11] Patent Number: 5,913,828
[45] Date of Patent: Jun. 22, 1999

[54] METHOD AND APPARATUS FOR DISTINGUISHING PACING PULSES IN AN EKG USING CONDUCTION VELOCITY CALCULATIONS

[75] Inventor: James K. Russell, McMinnville, Oreg.

[73] Assignee: Hewlett-Packard Company, Palo Alto, Calif.

[21] Appl. No.: 08/739,336

[22] Filed: Oct. 29, 1996

[51] Int. Cl.[6] ............... A61B 5/0452; A61B 5/0402; A61B 5/04
[52] U.S. Cl. .......................... 600/509; 600/508
[58] Field of Search .................. 128/696, 697; 600/508, 509, 510

[56] References Cited

U.S. PATENT DOCUMENTS

| | | |
|---|---|---|
| 3,780,727 | 12/1973 | King . |
| 4,141,367 | 2/1979 | Ferreira . |
| 4,522,208 | 6/1985 | Buffet . |
| 4,527,567 | 7/1985 | Fischler et al. ............ 128/697 |
| 4,543,963 | 10/1985 | Gessman . |
| 4,664,116 | 5/1987 | Shaya et al. . |
| 4,817,605 | 4/1989 | Sholder . |
| 4,838,278 | 6/1989 | Wang et al. . |
| 5,033,473 | 7/1991 | Wang et al. . |
| 5,215,100 | 6/1993 | Spitz et al. . |
| 5,411,529 | 5/1995 | Hudrlik . |
| 5,448,997 | 9/1995 | Kruse et al. . |
| 5,540,232 | 7/1996 | Laney et al. .............. 128/697 |
| 5,778,881 | 7/1998 | Sun et al. . |
| 5,833,621 | 10/1998 | Panescu et al. . |

*Primary Examiner*—William E. Kamm
*Assistant Examiner*—Carl H. Layno

[57] ABSTRACT

A method and device for distinguishing man-made electrical signals within a body from physiological electrochemical activity. The method and device work by detecting electrical signals within the body, and distinguishing the man-made electrical signals from the physiological electrochemical activity by calculating conduction velocities for the detected electrical signals. In distinguishing the signals, at least one pair of points where the electrical signals are being detected is designated as being of interest. At each point within this pair, the occurrence of the arrival times of each electrical signal is observed. On the basis of these observed arrival times, the signal is then determined to be either man-made or electrophysiological in origin.

13 Claims, 4 Drawing Sheets

METHOD AND APPARATUS FOR DISTINGUISHING PACING PULSES IN AN EKG USING CONDUCTION VELOCITY CALCULATIONS

BACKGROUND

1. Technical Field

The present invention relates, in general, to an improved bioinstrumentation signal-processing system and, in particular, to an improved bioinstrumentation signal-processing system having the ability to distinguish man-made electrical signals within the body from physiological electrochemical activity. Still more particularly, the present invention relates to an improved bioinstrumentation signal processing system having the ability to distinguish man-made electrical activity within the body from physiological electrochemical activity by calculating the conduction velocities of detected electrical signals.

2. Description of the Related Art

The heart pumps blood by organized successive contraction of individual heart muscle fibers. A neurological signal spreads through the heart, and each muscle fiber responds by contracting in sequence. The overall effect is a single heartbeat, or heart pulse, moving blood through the heart. For effective pumping, the muscle fibers must contract in an organized fashion.

The neurological signal alluded to in the previous paragraph is effectuated by the spread of an action potential throughout the heart. An action potential is a transient change in cell membrane potential which conveys information, such as the information in a signal telling a heart muscle fiber to contract. When the heart muscle is at rest, the electrical potential on either side of any cell membrane is maintained at a fixed potential. However, when the muscle is stimulated, either electrically, chemically, or mechanically, channels open in the membrane which allow the oppositely charged ions on either side of the membrane to cross the membrane, such ions engaging in an effort to reach electrical and thermal neutrality. This occurrence is referred to as "depolarization" since the system is becoming less polarized as the ions tend toward the lowest energy state. If the stimulation is great enough, the change in potential arising from the ions crossing the membrane will be great enough to depolarize the portion of the membrane directly adjacent to the area of the membrane depolarized by the stimulus. When this occurs, an action potential is said to have been initiated, and the signal will continue to propagate through the fiber via the just described mechanism of depolarizing that portion of the membrane directly adjacent to the depolarized area. This propagation of the action potential is analogous to the way in which a row of dominoes falls when the first is flicked into the second, and the second falls into the third, and the third falls into the fourth, etc. Once the action potential has propagated past a region of the membrane, the cell membrane resets itself in a process known as "repolarization." In repolarization, ions are actively pumped back across the cell membrane to restore the polarized state.

In addition to the ions involved in the propagation of the action potential, there are numerous other free-floating ions distributed throughout the body. These ions will move under the influence of sufficiently strong electric fields. When the action potentials within the heart propagate, the ions moving across the cell membrane will disturb the electric fields within the body. This physiological electrochemical activity can be conducted to the body's surface via the reaction of the free-floating ions, which move in response to the electric-field effect of the charges crossing the membrane.

In the late 1800s, the Dutch physiologist Dr. Willem Einthoven developed techniques for recording this electrical activity of the heart, for which he was awarded a Nobel prize. The basic technique of Dr. Einthoven is still in use today. Dr. Einthoven's technique is known as the electrocardiogram, which is still referred to in honor of Dr. Einthoven as the EKG, which arises from the Dutch spelling of electrocardiogram.

During an EKG, electrodes are attached to the body surface. The electrodes are specially treated to allow the charge carrier within the electrodes (electrons) to communicate with the charge carriers within the body (ions) via electrochemical exchange. Attaching electrodes to the body surface allows the voltage changes within the body to be recorded after adequate amplification of the signal. A galvanometer within the EKG machine is used as a recording device. Galvanometers record potential differences between two electrodes. The EKG is merely the recording of differences in voltage between two electrodes on the body surface as a function of time, and is usually recorded on a strip chart. When the heart is at rest, diastole, the cardiac cells are polarized and no charge movement is taking place. Consequently, the galvanometers of the EKG do not record any deflection. However, when the heart begins to propagate an action potential, the galvanometer will deflect since an electrode underneath which depolarization has occurred will record a potential difference from a region on the body under which the heart has not yet depolarized.

A complete heart cycle is known as a heartbeat. On an EKG, the heartbeat has a distinctive signal. Initially, the galvanometer notes a small but sharp negative deflection (known as the Q wave). Next, there is a very large and sharp positive deflection (known as the R wave), after which there is a sharp and large negative deflection (known as the S wave). When these waves are taken together, they are known as the QRS complex.

The EKG, in practice, uses many sets of electrodes. But these electrodes are so arranged on the surface of the body such that the signal received will have the same shape as that just described. Well-known bipolar pairs of electrodes are typically located on a patient's right arm (RA), left arm (LA), right leg (RL) (commonly used as a reference), and left leg (LL). Monopolar electrodes referenced properly are referred to as V leads and are positioned anatomically on a patients chest according to an established convention. In heart monitoring and diagnosis, the voltage differential appearing between two such electrodes or between one electrode and the average of a group of other electrodes represents a particular perspective of the heart's electrical activity and is generally referred to as the EKG. Particular combinations of electrodes are called leads. For example, the leads which may be employed in a standard twelve-lead electrocardiogram system are:

Lead I=(LA−RA)
Lead II=(LL−RA)
Lead III=(LL−LA)
Lead V1=V1−(LA+RA+LL)/3
Lead V2=V2−(LA+RA+LL)/3
Lead V3=V3−(LA+RA+LL)/3
Lead V4=V4−(LA+RA+LL)/3
Lead V5=V5−(LA+RA+LL)/3
Lead V6=V6−(LA+RA+LL)/3
Lead AVF=LL−(LA+RA)/2

Lead AVR=RA−(LA+LL)/2

Lead AVL=LA−(RA+LL)/2

Thus, although the term "lead" would appear to indicate a physical wire, in electrocardiography the term actually means the electrical signal taken from a certain electrode arrangement as illustrated above.

As alluded to above, the action potential which results in the contraction and beating of the heart has to be initiated by some agent. In the normal heart, this initiation is supplied by the sinoatrial node acting through the atrioventricular node. That is, the sinoatrial-atrioventricular complex acts to pace the firing of the heart muscle. However, in some instances, these natural pacemakers do not work correctly, and in those instances, control of cardiac activity by electric signal has proven to be useful.

The electric signal necessary is supplied by a pacing signal generator, which connects to the heart by a pair of pacing electrodes—a positive conductor and a negative conductor. The pacing generator takes the place of the body's malfunctioning natural pacemaker, and maintains a constant pulse rate by application of an electric pacing signal to the heart. The pacing signal provides an electric pulse, which gives rise to an organized contraction of the heart muscle fibers throughout the heart, thus causing the heart to beat. In other words, a pacing signal is a regulating signal for maintaining constant and effective pumping action by the heart.

For various reasons, medical professionals need to be able to view EKG data, even for a person with an electrical pacemaker. Unfortunately, for the same reasons that the EKG works, when the mechanical pacemaker discharges, it shows up as a deflection on an EKG. Furthermore, since the electrical pacemaker often discharges as a pulse of short time-duration, one can see that if the QRS complex is also of very short duration, which is very often the case for young pediatric patients and persons with various heart defects, it could be very difficult to select the pace pulse data from the QRS complex of the EKG. Thus, a need exists for a device which can easily and efficiently do this.

This need has not been satisfied, nor even generally recognized, in the prior art, as will be shown by the following summary of prior art references.

Wang et al (U.S. Pat. No. 4,838,278) disclose an apparatus for classifying the QRS complexes within EKG waveforms as dual-chamber paced, atrially paced, ventricularly paced, or unpaced, which is accomplished by comparing each acquired QRS complex with multiple pathologic QRS complexes stored in memory and making the assessment based upon pattern-matching between the acquired and stored complexes. Although Wang et al. recognize the difficulty in determining when a QRS complex and pacing pulse occur, Wang et al's disclosed apparatus utilizes a conventional pace pulse detector and conventional QRS detector to classify a QRS complex based upon the interval between the pacing pulse and the QRS complex. This reference does not consider nor discuss discriminating pace pulse data from EKG data that closely resemble pace-pulse data when measured by a single lead.

Wang et al. (U.S. Pat. No. 5,033,473) disclose a method and apparatus for discriminating between pace pulses and QRS complexes by determining whether a potential pace pulse tail exhibits an exponential decay in amplitude. Furthermore, this reference relates to detection of a largely obsolete form of pace pulse (with exponential tail). The present invention is not limited to this largely obsolete form of pace pulse. This reference does not consider nor discuss pulling pace pulse data from EKG data when they overlap very closely in time.

Kruse et al. (U.S. Pat. No. 5,448,997) disclose a pace pulse detector which utilizes multiple EKG leads to obtain a view of the heart from multiple angles. The pace pulse detector disclosed by Kruse et al. employs an algorithmic approach to pace-pulse discrimination which utilizes analog and digital filtering and signal processing to compare EKG waveform features with known amplitudes and spacings of pacing pulses. EKG waveform features matching the known amplitude and spacing characteristics of pacing pulses are then identified as pacing pulses. This reference does not consider nor discuss pulling pace-pulse data from EKG data when they overlap very closely in time; in fact, it appears that the method disclosed in this reference will not work if the pace pulse and the QRS complex are in identity, or very close thereto. Another distinction between the pace synchrony detector and the Kruse et al. patent is that the pace synchrony detector uses simultaneous information from multiple leads to develop information about conduction velocity, while the Kruse et al. patent uses multiple leads only to allow the selection of a single "best lead", after which this single lead is treated with conventional methods (pace width analysis primarily).

Sholder et al. (U.S. Pat. No. 4,817,605) discloses a pacemaker apparatus for achieving and maintaining atrial (P-wave) capture The output of the apparatus enables the monitoring of pacing pulses and P-waves, thereby enabling a physician to determine if atrial capture has been achieved by examining the time differential between the pacing pulses and the P-waves. Sholder et al. further discloses that the time differential between the pacing pulses and P-waves can be utilized to determine if a P-wave is generated in response to a pacing pulse or the activity of the sinus node of the heart utilizing known signal propagation characteristics of the heart. This reference does not consider nor discuss pulling pace-pulse data from EKG data when they overlap very closely in time. In fact, Sholder et al's patent refers to another class of apparatus, integrated with the pacemaker itself and having a prior knowledge of the timing of pace pulses. It is not really comparable with the problem of discriminating pace pulses from an ECG recording without this knowledge.

Shaya et al. (U.S. Pat. No. 4,664,116) disclose a pace-pulse identification apparatus which discriminates pacing pulses from other EKG wave features, including QRS complexes, on the basis of amplitude. Shaya et al's patent is fairly straight forward example of the class of detector the pace pulse synchrony detector improved upon by taking advantage of simultaneous lead information to calculate conduction velocities. This reference does not consider nor discuss pulling pace-pulse data from EKG data when they overlap very closely in time; in fact, it appears that the method disclosed in this reference will not work if the pace pulse and the QRS complex are in identity with respect to either time or amplitude.

As noted above, several of the references discovered by the search disclose systems which discriminate between pacing pulses and various waveform features, including QRS complexes. However, in contrast to the present invention, none of these disclose how to separate man-made pulses from the EKG data when the EKG has extremely narrow QRS complexes, such as are found in pediatric patents. Or, restated none of these disclose how to separate man-made pulses from the EKG data when the temporal or and frequency characteristics of the EKG data closely resemble man-made pulses.

In view of the foregoing, it should be apparent that a need exists for the present invention: an improved bioinstrumentation signal-processing system which can distinguish man-made electrical signals within the body from physiological electrochemical signals within the body when the man-made signals can overlap in time, and thus mimic, the physiological electrochemical activity within the body.

SUMMARY

It is therefore one object of the present invention to provide an improved bioinstrumentation signal-processing system.

It is another object of the present invention to provide an improved bioinstrumentation signal-processing system having the ability to distinguish man-made electrical signals within the body from physiological electrochemical activity.

It is yet another object of the present invention to provide an improved bioinstrumentation signal-processing system having the ability to distinguish man-made electrical activity within the body from physiological electrochemical activity by calculating the conduction velocities of detected electrical signals.

The foregoing objects are achieved as is now described. A method and device are provided for distinguishing man-made electrical signals within a body from physiological electrochemical activity. The method and device work by detecting electrical signals within the body and distinguishing the man-made electrical signals from the physiological electrochemical activity by calculating conduction velocities for the detected electrical signals between various points. In distinguishing the signals, at least one pair of points where the electrical signals are being detected is designated as being of interest. At each point within this pair, the occurrence of the arrival times of each electrical signal is observed. On the basis of these observed arrival times, conduction velocities are calculated, and the signal is then determined to be either man-made or electrophysiological in origin.

The above as well as additional objects, features, and advantages of an illustrative embodiment will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION

The present invention is a method and device for distinguishing man-made electrical signals within a body from physiological electrochemical activity. The method and device work by detecting electrical signals within the body and distinguishing the man-made electrical signals from the physiological electrical activity by calculating conduction velocities for the detected electrical signals.

In biomedical devices, the term "conduction velocity" can mean one of two things: (1) the term can refer to the actual time it takes for electrical energy to travel from an electrical source to an electrical sink through the medium of a volume conductor, such as blood, located within the body; or (2) the term can refer to the time it takes for an action potential, which is a transient change in the membrane potential that conveys information within the nervous system, to propagate from one location to another over the paths along which the action potential can travel. The present invention utilizes the fact that the conduction velocity of electrical energy through a volume conductor is different from the conduction velocity of action potentials along cells which can propagate action potentials. Consequently, the term "conduction velocity" as utilized herein, will refer to a composite concept which is derived from and relies upon the two foregoing meanings.

The term conduction velocity as utilized herein will be used in its operational sense. That is, the term conduction velocity will refer to how quickly electrical signals make themselves known at different locations at, on, or within the body. Specifically, as used in this specification, the term conduction velocity will refer to the distance between points divided by the time it takes for a signal to make itself known at first one point and then the other. That is, in the present invention, which is based upon the difference in the conduction velocities of an electrical signal within a volume conductor and an electrochemical signal within a nerve fiber or heart-muscle fiber, those mechanisms are not overtly utilized when referring to the operational description of the invention. Instead, we view the occurrence of the signal at different points on the body surface, and refer to the time it takes to travel between two points as conduction velocity.

The present invention makes use of the fact that conduction through the volume conductor occurs virtually instantaneously, while the propagation of action potentials along their respective channels requires a considerably longer period of time. In conjunction with this fact, the present invention also uses knowledge that a man-made electrical device discharged within the body gives rise to much greater energy than the discharge of an action potential. The present invention utilizes this knowledge, in conjunction with the foregoing-cited properties related to conduction within the volume conductor as opposed to conduction of action potentials, to discriminate between electrical signals within the body which arose from man-made devices and electrical signals within the body which arose from the electrochemical activity associated with the propagation of action potentials. The present invention does this by recognizing that the much higher energy discharge of the man-made device will ensure that its electrical effects can be sensed virtually simultaneously by electrodes placed at varying points along the body, while the electrical activity created by the propagation of an action potential will only be detectable within a very short distance from that action potential. It should be understood that once the action potential reaches a point near the sensing electrode, it must still propagate to that electrode under the physical constraints of volume conduction. Thus, with a QRS complex, the conduction time is the sum of a physical propagation time and a physiological propagation time.

The present invention makes use of the foregoing facts by deeming electrical signals, which appear virtually instantaneously in all regions within the body, to be man-made signals, while deeming electrical signals which appear at different points of the body, only delayed by various increments in time, as being those arising from electrochemical activity within the body.

Figure 1:
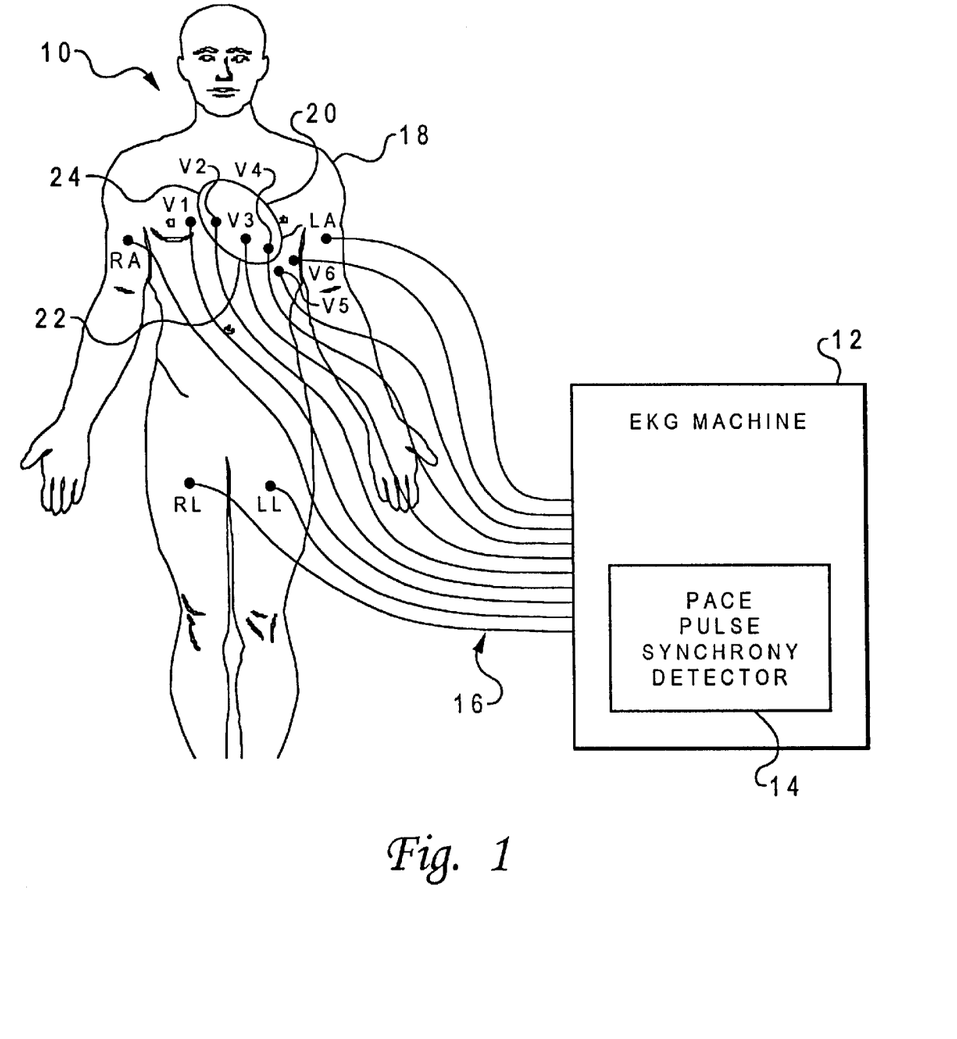
FIG. 1 illustrates a high-level schematic view of a system for implementing the present invention.

With reference now to the figures and, in particular, with reference to FIG. 1, there is depicted a high-level schematic view of a system for implementing the present invention. Depicted is a body 18 to which a number of electrocardiographic electrodes 10 have been attached. Also depicted is a representation of the heart 20 having both an apex 22 and a base 24. The electrocardiographic electrodes 10 are shown as arranged such that the standard 12-lead electrocardiogram (EKG) can be captured. With respect to this standard EKG arrangement, note that certain of the electrocardiographic electrodes 10, are proximate to the apex of the heart 22, and others are proximate to the base of the heart 24. As used herein, the term proximate means that the electrodes are electrically close to the heart; in other words, any electrochemical activity will be nearly instantaneously transmitted to those electrodes deemed electrically close through the volume conductor. The electrocardiographic electrodes 10 are depicted as connecting to an EKG machine 12 via conducting wires 16. Also depicted is the preferred embodiment, the pace-pulse synchrony detector 14, which is depicted as being enclosed within the EKG machine 12 itself. However, it is not intended that such is the only implementation for this invention but, rather, this is one way in which the invention could be used.

Figure 2:
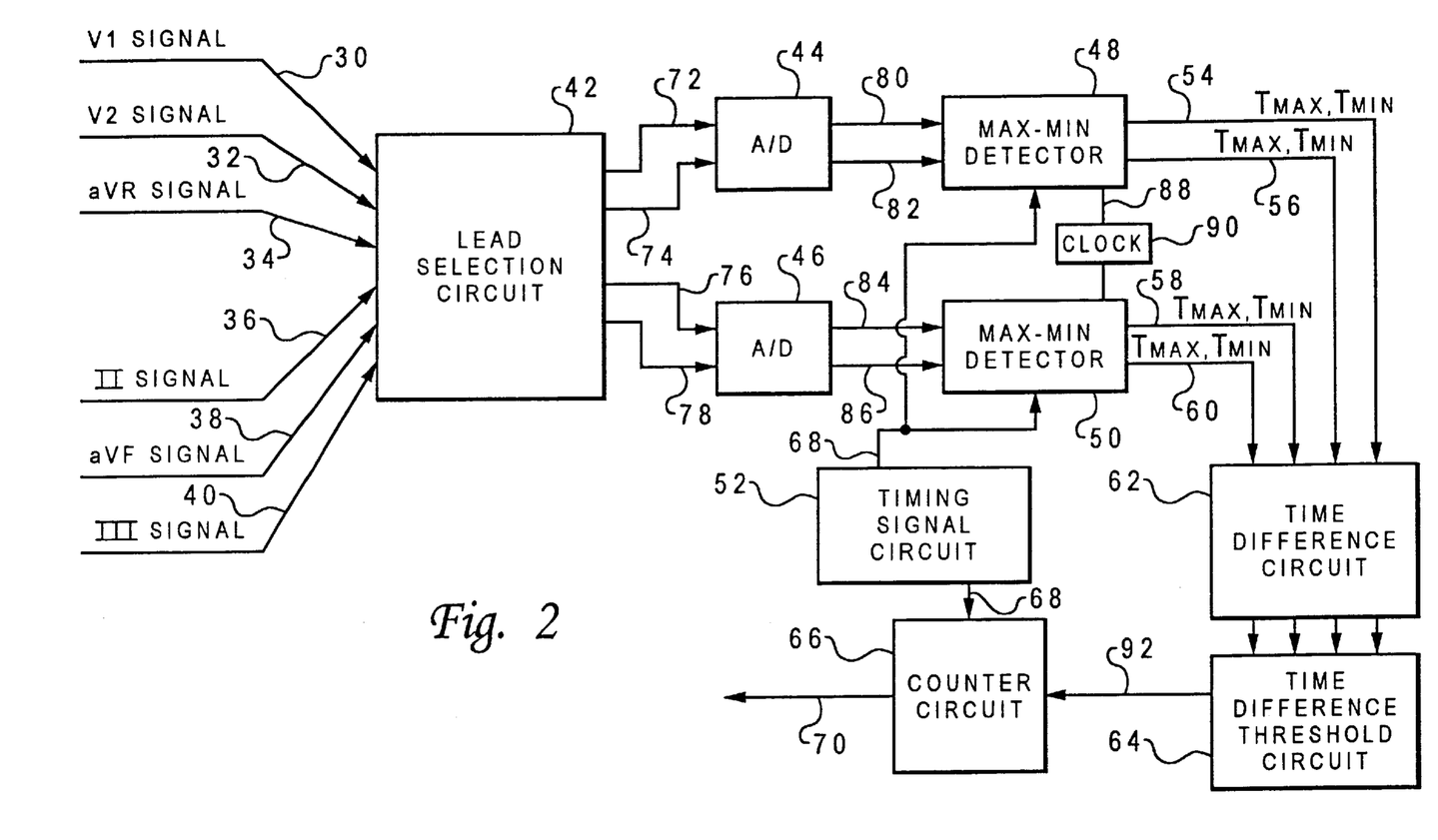
FIG. 2 is a high-level block diagram of the Pace Pulse Synchrony Detector of FIG. 1.

Referring now to FIG. 2, there is depicted a high-level block diagram showing the logic involved in the invention. Shown are three input signals corresponding to three specific leads (keep in mind that the term lead means signal from an arrangement of electrodes) of the EKG. Specifically, Lead V1 30, Lead V2 32, and Lead AVR 34 are shown together and are taken as forming a first set. As can be seen in FIG. 1, the probe electrodes of these leads are proximate to the base of the heart. Therefore, they are referred to as basal leads. Further referring to FIG. 2, Lead II 36, Lead AVF 38, and Lead III 40 are shown together and are taken as forming a second set. The measuring electrodes of these leads can be seen, in FIG. 1, to be proximate to the apex of the heart. Therefore, they are referred to as apical leads. These six leads feed into a lead selection circuit 42, which examines the signal strength on each of the leads and selects a subset of two leads out of the set formed by Lead V1 30, Lead V2 32, and Lead AVR 34 on the basis of signal strength. The lead selection circuit 42 repeats this operation for the set formed by Lead II 36, Lead AVF 38, and Lead III 40, in that the lead selection circuit 42 examines the signal strength of each of these three leads and selects a subset of two of them on the basis of signal strength. The leads so selected is designated in the figure as basal signal 1 72, basal signal 2 74, apical signal 1 76, and apical signal 2 78. The basal signals are then fed into an analog-to-digital converter 44 which outputs a digitized version of basal signal 1 80, and a digitized version of basal signal 2 82. In addition, the apical signals are fed into another analog-to-digital converter 46 which outputs the digitized version of apical signal 1 84 and the digitized version of apical signal 2 86.

The digitized versions of the basal signals are then fed into a maximum-minimum detector 48, which is controlled by a timing signal 68, which is generated by a timing-signal circuit 52. The timing signal 68 causes the maximum-minimum detector 48 to begin to examine both the digitized version of basal signal 1 80 and the digitized version of basal signal 2 82. The maximum-minimum detector 48 observes the digitized versions of both signals and records the time at which those signals reach maximum and minimum values; that is, the maximum-minimum detector 48 records the time when the digitized version of basal signal 1 80 hits its maximum value and its minimum value, and the maximum-minimum detector 48 also records the time at which the digitized version of basal signal 2 82 hits its maximum and its minimum values. The detector will continue to do this operation until the timing-signal circuit 52 indicates via timing signal 68 that the window of time is to be closed, at which point the maximum-minimum detector outputs one signal 54 containing data corresponding to the times at which the maximum value and the minimum value of the digitized version of basal signal 1 80 occurred, and outputs another signal 56 corresponding to the times at which the maximum value and the minimum value of the digitized version of basal signal 2 82 occurred. The maximum-minimum detector 48 is able to keep track of the time of occurrence via a clock signal 88 supplied from a clock 90.

Simultaneous with the processing of the basal signals as described in the previous paragraph, the apical signals are processed in exactly the same way. That is, the digitized versions of the apical signals 84, 86 are fed into a maximum-minimum detector 50, which is controlled by a timing signal 68, which is generated by a timing-signal circuit 52. The timing signal 68 causes the maximum-minimum detector 50 to begin to examine both the digitized version of apical signal 1 84 and the digitized version of apical signal 2 86. The maximum-minimum detector 50 observes the digitized versions of both signals and records the time at which those signals reach maximum and minimum values; that is, the maximum-minimum detector 50 records the time when digitized version of apical signal 1 84 hits its maximum value and its minimum value, and the maximum-minimum detector 50 also records the time at which the digitized version of apical signal 2 86 hits its maximum and its minimum values. The detector will continue to do this operation until the timing-signal circuit 52, indicates via the timing signal 68, that the window of time is to be closed, at which time the maximum-minimum detector outputs one signal 58 corresponding to the times at which the maximum value and the minimum value of the digitized version of apical signal 1 84 occurred, and outputs another signal 60 corresponding to the times at which the maximum value and the minimum value of the digitized version of apical signal 2 86 occurred. The maximum-minimum detector 50 is able to keep track of the time of occurrence via a clock signal 88 supplied from a clock 90.

The eight foregoing-noted times corresponding to different maximums and minimums of different leads are then fed into the time-difference circuit 62. The time-difference circuit 62 calculates the amount of time which elapses between the appearance of a maximum at one of the basal leads versus the time of the appearance of a maximum at one of the apical leads. For example, one such time difference would be determined by taking the time at which the maximum of basal lead 1 occurred, and subtracting from it the time at which the maximum of basal lead 2 occurred; the absolute value of the result of this subtraction is then determined, and this will represent the time difference between the appearance of the maximum of the signals appearing at the measuring electrodes of basal lead 1 and apical lead 1. As another example, the time at which the minimum of basal lead 2 occurred is subtracted from the time at which the minimum of apical lead 2 occurred; the absolute value of this quantity is then taken, and this is then the time difference between the appearance of the minimum of the signals at the measuring electrodes of apical lead 1 and apical lead 2. Similar operations are performed for all possible combinations of basal and apical leads, and the calculated time differences are then stored. The time-difference circuit 62 then passes these time differences to the time-difference threshold circuit 64. The time-difference threshold circuit 64 then compares each of the time differences calculated by the time-difference circuit 62 to a predetermined time-difference threshold, and for each of the calculated time differences, which is less than the predetermined time-difference threshold, the time-difference threshold circuit 64 outputs a within-threshold-limit signal 92 which causes the counter 66 to increment. The counter 66 is reset to zero during each new window of time by the timing-control circuit 52, via the timing-control signal 68, and thus yields a new count for each window of time. Once all time differences have been compared by the time-difference threshold circuit 64, the counter circuit 66 compares the total number counted, which represents the total number of differences in time which were less than the predetermined time-difference threshold, and compares that total count to a predetermined number. If that predetermined number is met or exceeded, the counter circuit 66 classifies the signal as being of man-made origin and outputs a signal indicating such on its output line 70.

Figure 3A:
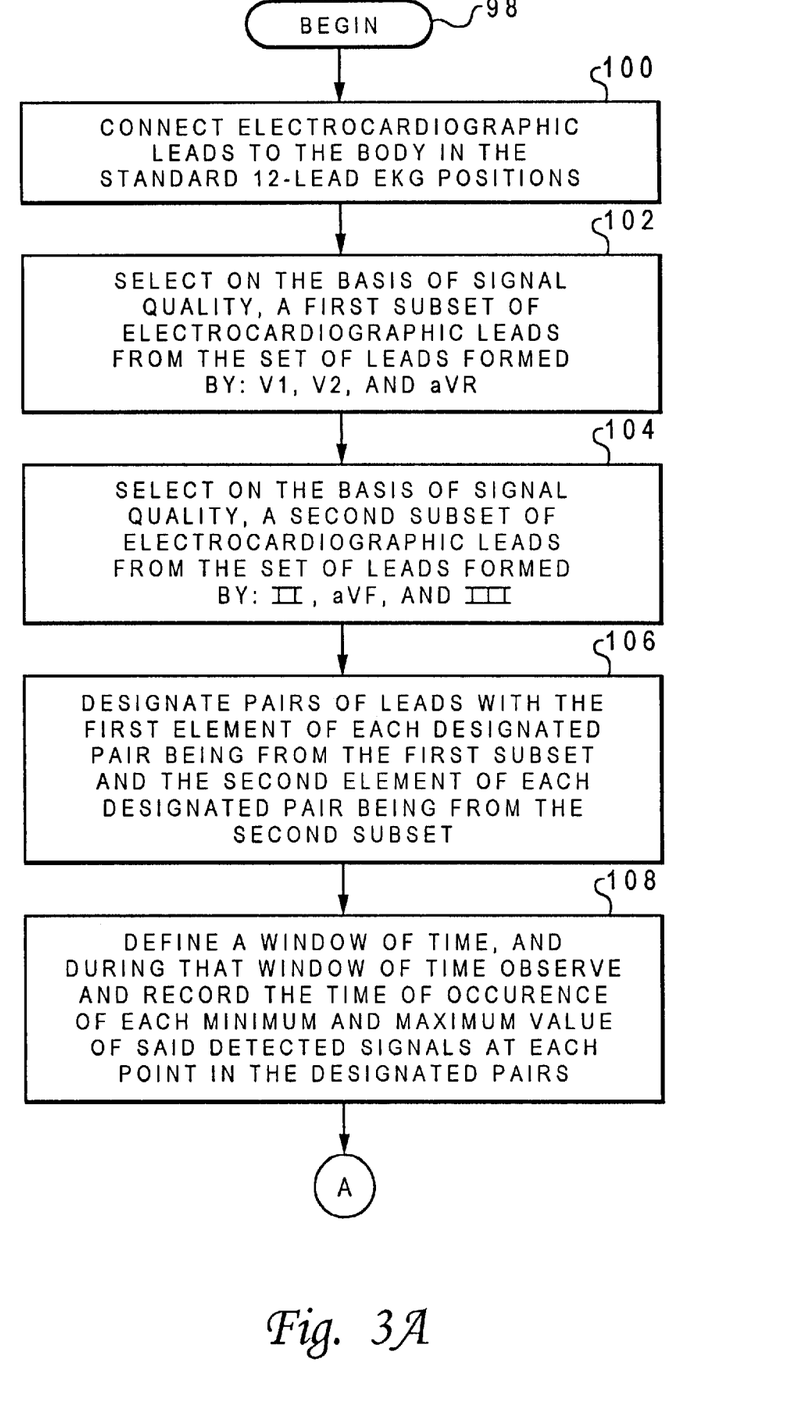
FIGS. 3A and 3B are a high-level logic flowchart of an illustrative embodiment of the method whereby the Pace Pulse Synchrony Detector of FIG. 1 distinguishes man-made electrical signals from physiological electrochemical activity.
Figure 3B:
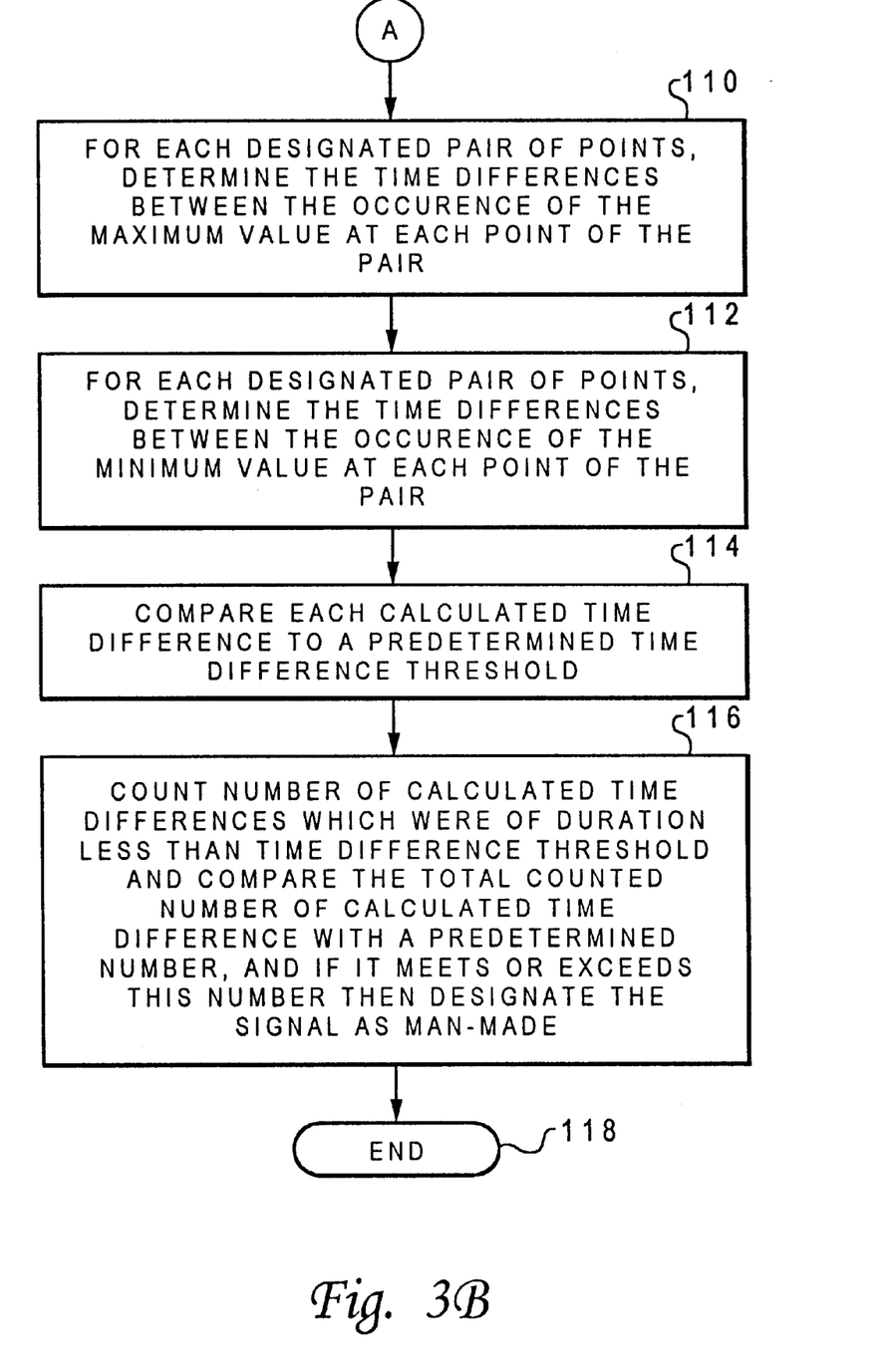

With reference now to FIG. 3, there is depicted a high-level logic flowchart whereby man-made electrical signals within the body are distinguished from physiological electrochemical activity. Step 98 shows the beginning of this process. Step 100 depicts the method step wherein a number of electrocardiographic electrodes are connected to the external surface of the body such that an electrocardiographic signal can be obtained and such that at least one of the electrodes is proximate to the apex of the heart and such that one is proximate to the base of the heart; furthermore, this step also includes the possibility that additional electrodes could be connected such that redundant pairs of the electrodes are formed, with the first element of each redundant pair being proximate to the apex of the heart and the second element being proximate to the base of the heart.

Step 102 illustrates the method step of a selection, on the basis of signal quality, of a first subset of electrocardiographic leads from a first set of leads formed by Lead V1 30, Lead V2 32, and Lead AVR 34, as those terms are defined earlier in this specification; these leads are referred to as basal since the measuring electrodes of these leads are proximate to the base of the heart 24. Step 104 depicts the selection, on the basis of signal quality, of a second subset of electrocardiographic leads from the second set of leads formed by Lead II 36, Lead AVF 38, and Lead III 46; these leads are referred to as apical since the measuring electrodes of these leads are proximate to the apex of the heart.

Method step 106 depicts the designation of pairs of leads wherein the first element of the pair is taken from the previously defined first subset, and the second element of the pair is taken from the previously defined second subset; that is, the first lead of the pair is taken from the basal leads set, and the second lead of the pair is taken from the apical leads set. This allows the designation of pairs of leads such that one of the leads forming the pair is measured from a position proximate to the apex of the heart, and one of the leads forming the pair is measured from a position proximate to the base of the heart. Method step 108 illustrates the definition of a window of time, during which the electrical signals are to be observed at all of the leads forming the aforementioned designated pairs of Leads.

Method Step 108 also illustrates, during the defined window of time, and the actions of both observing and recording the time at which the maximum occurs and the minimum occurs for each lead within the foregoing-described designated pairs of leads. Method step 110 depicts, for each defined window of time, the determination of the time differences between the occurrences of the maximum values for each of the two leads within the designated pairs. Method step 112 depicts, for each defined window of time, the determination of the time differences between the occurrences of the minimum values at each of the leads within the designated pairs of leads.

Method step 114 depicts the comparison of each of the aforementioned calculated time differences to a predetermined time-difference threshold. This predetermined time-difference threshold represents a measure of synchrony; that is, if the calculated time difference is less than the predetermined time-difference threshold, then this is taken to be an indication of a measure of synchrony of the signals. Method step 116 depicts the operation of counting the number of calculated time differences that the preceding method step 114 indicated were less than the predetermined time-difference threshold.

Method step 116 further depicts that the total count of the number of time differences that were less than the predetermined time-difference threshold is compared to a predetermined number, and if the count meets or exceeds this predetermined number, then the signal observed during the aforementioned window of time is designated to be a man-made signal. Method step 118 illustrates the end step of the method wherein man-made signals are distinguished from physiological electrochemical activity within the body.

While an illustrative embodiment has been particularly shown and described, it will be understood by those skilled in the art that various changes in form and detail may be made therein without departing from the spirit and scope of the illustrative embodiment.

What is claimed is:

1. A method for distinguishing non-physiological electrical signals within a body from physiological electrochemical activity, said method comprising the steps of:

connecting a plurality of electrodes to the external surface of the body such that electrical signals within said body can be detected;

detecting, at a plurality of points, electrical signals within the body; and distinguishing non-physiological electrical signals from physiological electrochemical activity by calculating conduction velocities of said detected electrical signals between selected pairs of said plurality of points.

2. The method of claim 1, wherein said step of distinguishing further comprises the steps of:

designating at least one of said selected pairs of points;

determining arrival times of one of said electrical signals at each individual point of said at least one designated pair of points;

comparing said arrival times of said one of said electrical signals at each of said individual points; and in response to said comparison, determining whether said one of said electrical signals is either man-made or the result of said physiological electrochemical activity.

3. The method of claim 1, said body including a heart having both an apex and a base, wherein said step of connecting a plurality of electrodes to said external surface of the body further comprises the step of connecting said plurality of electrodes such that an electrocardiographic signal can be obtained and such that at least one of said plurality of electrodes is proximate to the apex of the heart and such that at least one of said plurality of electrodes is proximate to the base of the heart.

4. The method of claim 1, wherein said step of distinguishing man-made electrical signals from physiological electrochemical activity by calculating conduction velocities of said detected electrical signals between selected pairs of said plurality of points wherein said selected pairs can be selected by the method comprised of the following steps:

connecting a plurality of electrodes to said external surface of said body such that redundant pairs are formed and such that for each of said redundant pairs a first electrode of said redundant pair is proximate to the apex of the heart and a second electrode of said redundant pair is proximate to the base of the heart;

selecting, on the basis of signal quality, a first subset of electrodes from a set formed by said first electrodes of said redundant pairs;

selecting, on the basis of signal quality, a second subset of electrodes from a set formed by said second electrodes of said redundant pairs; and creating said selected pairs of said plurality of points such that the first electrode in said designated pair is a member of said first subset and that the second electrode in said designated pair is a member of said second subset.

5. The method of claim 2 wherein said steps of determining and comparing the arrival times of said one of said electrical signals at each of said single points further comprises the step of:

establishing, for each of said at least one designated pair of points, a window of time during which said one of said electrical signals at each individual point of said at least one designated pair of points will be observed;

determining, during said window of time, the time at which the minimum and maximum of said one of said electrical signals occurs at each said individual point of said at least one designated pair of points;

calculating the difference between said time of occurrence of the minimum of said one of said electrical signals at each individual point of said at least one designated pair of points; and calculating the difference between said time of occurrence of each maximum of said one of said electrical signals at each individual point of said at least one designated pair of points.

6. The method of claim 5, wherein said step of determining whether said one of said electrical signals is either man-made or the result of said physiological electrochemical activity further comprises the steps of:

counting, for each of said at least one designated pair of points, the number of said calculated differences which said comparison indicated is smaller than a predetermined time difference threshold; and comparing said counted number of said time differences with a predetermined number, and designating said one of said electrical signals observed during said window of time as man-made if said counted number of time differences is greater than said predetermined number.

7. A device for distinguishing non-physiological electrical signals within a patient's body, from physiological electrochemical activity, said device comprising:

means for detecting, at a plurality of points, electrical signals within the body; and means for distinguishing non-physiological electrical signals from physiological electrochemical activity by calculating conduction velocities of said detected electrical signals between selected pairs of said plurality of points.

8. The device of claim 7, wherein said means of distinguishing further comprises:

means for designating at least one of said selected pairs of points;

means for determining arrival times of one of said electrical signals at each individual point of said at least one designated pair of points;

means for comparing said arrival times of said one of said electrical signals at each of said single points; and means for, in response to said comparison, determining whether said one of said electrical signals is either man-made or the result of said physiological electrochemical activity.

9. The device of claim 7, wherein said means for detecting comprises a means for connecting a plurality of electrodes to the external surface of the body such that electrical signals within said body can be detected.

10. The device of claim 9, said body including a heart having both an apex and a base, wherein said means for connecting a plurality of electrodes to the external surface of the body comprises the connecting of said plurality of electrodes such that an electrocardiographic signal can be obtained and such that at least one of said plurality of electrodes is proximate to the apex of the heart and such that at least one of said plurality of electrodes is proximate to the base of the heart.

11. The device of claim 7, wherein said means for distinguishing man-made electrical signals from physiological electrochemical activity by calculating conduction velocities of said detected electrical signals between selected pairs of said plurality of points wherein said selected pairs can be selected by a device comprising:

means for connecting a plurality of electrodes to said external surface of said body such that redundant pairs are formed and such that for each of said redundant pairs a first electrode of said redundant pair is proximate to the apex of the heart and a second electrode of said redundant pair is proximate to the base of the heart;

means for selecting, on the basis of signal quality, a first subset of electrodes from a set formed by said first electrodes of said redundant pairs;

means for selecting, on the basis of signal quality, a second subset of electrodes from a set formed by said second electrodes of said redundant pairs; and means for creating said selected pairs of said plurality of points such that the first electrode in said designated pair is a member of said first subset and that the second electrode in said designated pair is a member of said second subset.

12. The device of claim 8, wherein said means determining and comparing the arrival times of said one of said electrical signals at each of said single points is a device further comprising:

means for establishing, for each of said at least one designated pair of points, a window of time during which said one of said electrical signals at each individual point of said at least one designated pair of points will be observed;

means for determining, during said window of time, the time at which the minimum and maximum of said one of said electrical signals occurs at each said individual point of said at least one designated pair of points;

means for calculating the difference between said time of occurrence of the minimum of said one of said electrical signals at each individual point of said at least one designated pair of points; and means for calculating the difference between said time of occurrence of each maximum of said one of said electrical signals at each individual point of said at least one designated pair of points.

13. The device of claim 12, wherein said means for determining whether said one of said electrical signals is either man-made or the result of said physiological electrochemical activity further comprises the steps of:

means for counting, for each of said at least one designated pair of points, the number of said calculated differences which said comparison indicated are smaller than a predetermined time difference threshold; and means for comparing said counted number of said time differences with a predetermined number, and designating said one of said electrical signals observed during said window of time as man-made if said counted number of time differences is greater than said predetermined number.

* * * * *